(12) United States Patent
Hanke

(10) Patent No.: US 7,955,254 B2
(45) Date of Patent: Jun. 7, 2011

(54) MEDICAL VIDEOSCOPE WITH A PIVOTABLY ADJUSTABLE END PART

(75) Inventor: Harald Hanke, Hamburg (DE)

(73) Assignee: Olympus Winter & IBE GmbH, Hamburg (DE)

( * ) Notice: Subject to any disclaimer, the term of this patent is extended or adjusted under 35 U.S.C. 154(b) by 1100 days.

(21) Appl. No.: 11/695,347

(22) Filed: Apr. 2, 2007

(65) Prior Publication Data

US 2007/0238931 A1   Oct. 11, 2007

(30) Foreign Application Priority Data

Apr. 7, 2006   (DE) .......................... 10 2006 016 845

(51) Int. Cl.
*A61B 1/06* (2006.01)
*A61B 1/00* (2006.01)
(52) U.S. Cl. ........................................ 600/173; 600/142
(58) Field of Classification Search .................. 600/129, 600/141–142, 172–175, 101, 104
See application file for complete search history.

(56) References Cited

U.S. PATENT DOCUMENTS

| 5,692,668 | A | * | 12/1997 | Schulze et al. | ............. | 227/175.1 |
| 5,704,898 | A | * | 1/1998 | Kokish | ............. | 600/141 |
| 5,797,900 | A | * | 8/1998 | Madhani et al. | ............. | 606/1 |
| 5,989,182 | A | | 11/1999 | Hori et al. | | |
| 6,206,872 | B1 | * | 3/2001 | Lafond et al. | ............. | 606/1 |
| 6,450,950 | B2 | | 9/2002 | Irion | | |
| 6,916,286 | B2 | * | 7/2005 | Kazakevich | ............. | 600/173 |
| 7,670,334 | B2 | * | 3/2010 | Hueil et al. | ............. | 606/1 |
| 7,784,662 | B2 | * | 8/2010 | Wales et al. | ............. | 227/175.1 |
| 2002/0049367 | A1 | * | 4/2002 | Irion et al. | ............. | 600/173 |
| 2003/0032863 | A1 | * | 2/2003 | Kazakevich | ............. | 600/173 |
| 2003/0092966 | A1 | * | 5/2003 | Schara et al. | ............. | 600/173 |
| 2005/0234296 | A1 | * | 10/2005 | Saadat et al. | ............. | 600/129 |
| 2006/0189845 | A1 | * | 8/2006 | Maahs et al. | ............. | 600/146 |
| 2006/0199999 | A1 | * | 9/2006 | Ikeda et al. | ............. | 600/141 |

* cited by examiner

*Primary Examiner* — Philip R Smith
(74) *Attorney, Agent, or Firm* — Rankin, Hill & Clark LLP

(57) ABSTRACT

A medical endoscope including a stem (1) receiving in its distal end part (3) a video camera (30), the end part (3) being pivotably adjustable relative to the main part (2) of the stem (1) and connecting lines (27, 31) running in the stem (1) from a proximal end region to the end part (3), wherein the main part (2) and the end part (3) are enclosed in sealing manner by rigid stem tubes (5, 8) which are supported in an abutting and sealing manner in a joint (4) by means of a hollow axle (16, 18) running perpendicularly to the stem parts (2, 3), the hollow axle being crossed by the connecting lines (27, 31) in the inside spaces of the stem parts (2, 3).

9 Claims, 3 Drawing Sheets

MEDICAL VIDEOSCOPE WITH A PIVOTABLY ADJUSTABLE END PART

BACKGROUND OF THE INVENTION

1. Field of the Invention

The present invention relates to an endoscope having a stem receiving in its distal end part a video camera, the end part being pivotably adjustable relative to the main part of the stem.

2. Description of the Related Art

Known endoscopes of this kind are fitted with a flexible stem allowing for arbitrarily changing the spatial attitude of the end part. However, such flexible endoscopes incur known drawbacks. The flexible stem segment is internally very complex and covered outward by a flexible sheath. It suffers considerable sealing problems and there are foremost difficulties with cleaning and sterilization. Leaks and other malfunctions are frequent and require repairs. Moreover, when being touched, flexible endoscopes are susceptible to vibrate or jitter at the bent distal end and thereby substantially degrade image quality.

In this respect the rigid endoscopes, that is endoscopes fitted with a rigid stem tube, are considerably more advantageous. The stem tube encloses, in a well sealed manner, the internal space and makes possible simple cleaning and sterilization while also being operable in an essentially problem-free manner. On the other hand, rigid endoscopes to-date have precluded pivotable end parts. No more can be done than integrating an optics offering a pivoting field of view angle in the rigid end part. However this feature in turn entails optical and mechanical problems.

It is the objective of the present invention to create an endoscope of the above kind which is technically simple, less demanding of maintenance and less susceptible to malfunctions.

BRIEF SUMMARY OF THE INVENTION

In the present invention, both the stem's main and end parts are rigid and connected by a joint connecting the inner spaces of the two stem parts by means of a hollow axle. A sealed inner space running through the two stem parts is subtended in this manner and is crossed by the connecting lines, e.g. light-guides/electric-cables, from the proximal endoscope end zone to the end part. This design is technically simpler than using a flexible endoscope and allows easier cleaning and sterilization by eliminating the flexible, illustratively rubber sheath required in flexible endoscopes.

The two stem parts might be configured side by side, connected by the hollow axle. However, this design would entail doubling the cross-section in the joint zone. Accordingly, the stem parts subtend end segments at the joint that constitute each mutually abutting flat joint walls with a unilaterally cropped cross-section whereby the other shaft cross-section is not exceeded in the joint, because now the end segments each may abut one another having half the stem cross-section.

Joint sealing is advantageously implemented in that an O-ring seal configured around the hollow axle is mounted between the joint walls. This O-ring seal completely seals the joint. The joint requires no further sealing elements.

The hollow axle is advantageously designed in the manner that the hollow axle is affixed to one of the joint walls and crosses the other joint wall at an aperture and internally rests against the said wall by means of external flange. This design assures reliable connection between the two stem parts, which are easily assembled and disassembled. Screw affixation accessibility is advantageously implemented in that the screw system is accessible from the flange end of the hollow axle and in that a wall portion of the end segment may be deposited above the flange end of the hollow axle following assembly of the hollow axle by means of a detachable wall element, which, following joint assembly, shall be deposited and illustratively be sealed by welding or soldering.

Illustratively the end part may be pivoted by means of pull rods or the like, though advantageously, it shall be pivoted using a looping control cable.

The end segments may be integral with the tubes of the stem parts, however, they may be assembled as separate elements and illustratively may be welded together. This feature simplifies manufacture.

This design implements a mechanically strong and easily assembled joint using a hollow bolt allowing placement of the connecting lines.

The appended drawings show the present invention in an illustrative and schematic manner.

DETAILED DESCRIPTION OF THE INVENTION

Figure 1:
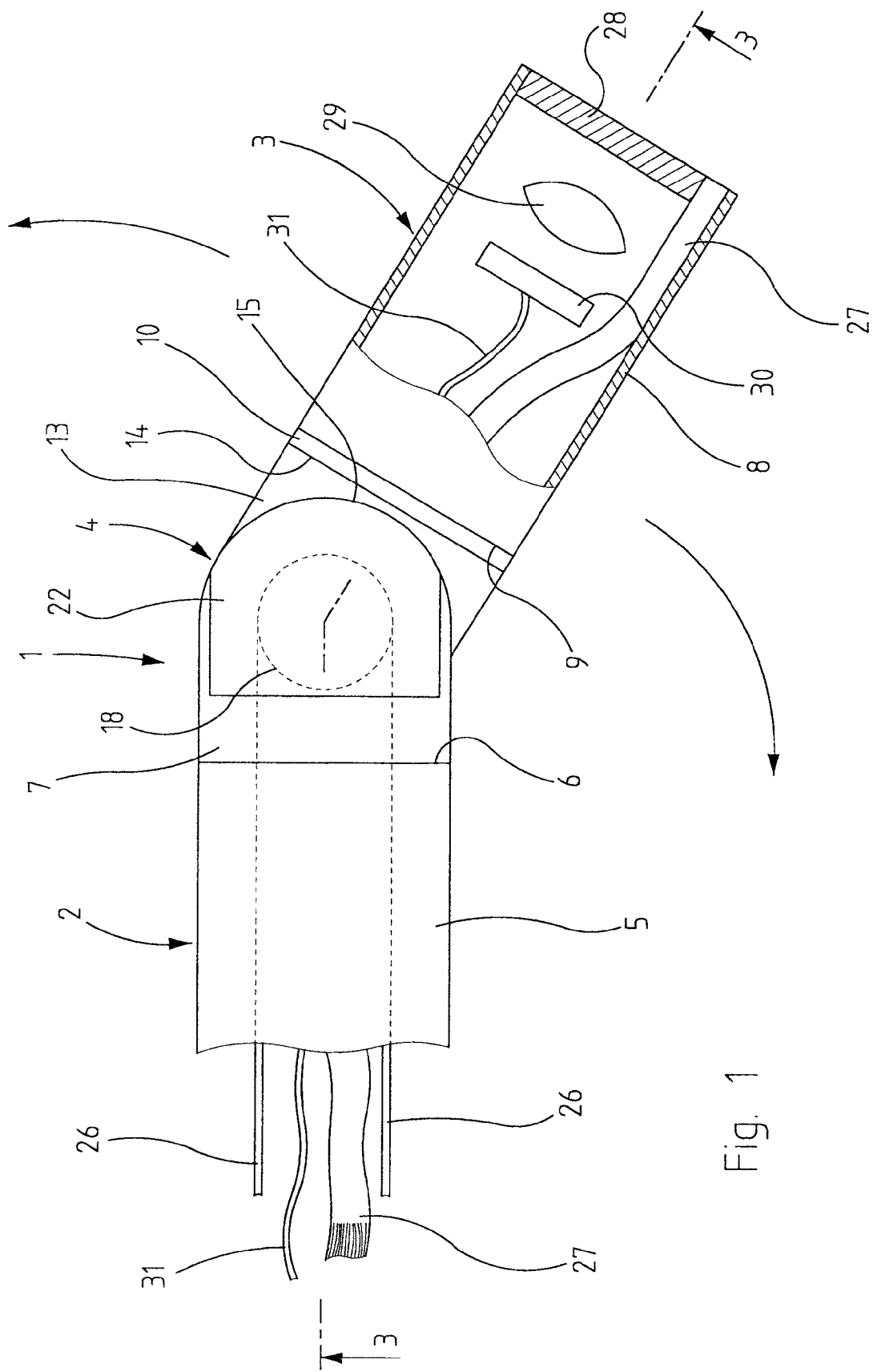
FIG. 1 is a topview of the end part and the region of the joint of an endoscope of the present invention.

FIG. 1 is a top view of the distal end part of the stem 1 of a medical video-scope comprising a main stem part 2 and a distal end part 3 which are connected by a joint 4.

The main part 2 comprises a straight, round rigid steel tube 5 of which the distal end 6 is connected, for instance, by welding to an end segment 7.

The end part 3 also is fitted with a rigid tube 8 of which the proximal end 9 is connected, for instance, by welding to an end element 10.

Each end segment 7, 10 comprises the cross-sectionally circular shape of the tube 5 resp. 8 at their connecting edges 11 while being cropped to half the tube cross-section in their remaining portion to subtend each a flat joint wall 12, 13 respectively situated at the center of said cross-section with which the end segments 7, 10 may rest flat, one on the other, in the joint region 4.

Figure 2:
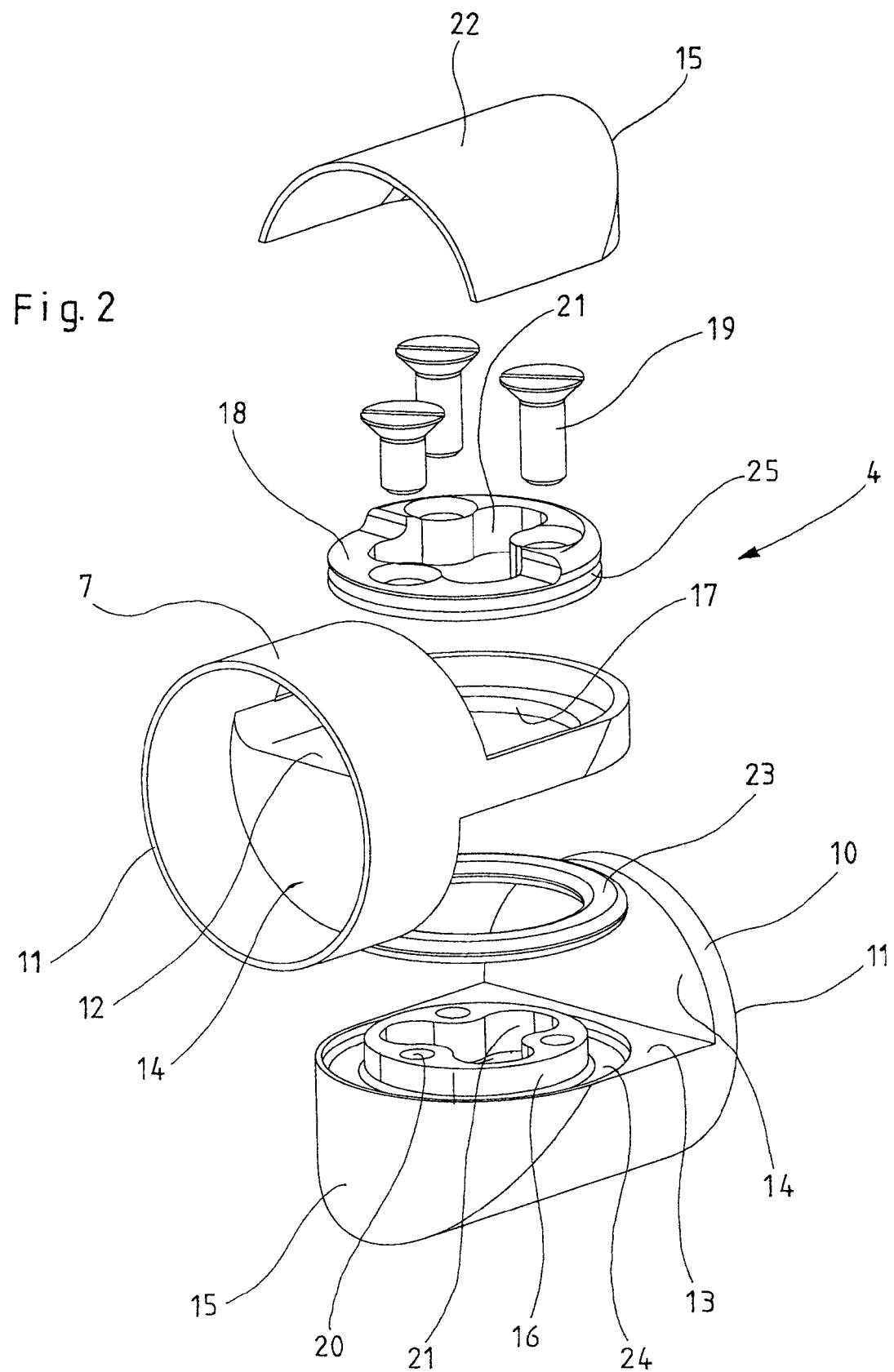
FIG. 2 is an exploded view of the said region of the joint.

The exploded view of FIG. 2 shows the components of the joint 4 separated from each other in the axial direction.

At the transition site between the circular tube cross-section and the cropped cross-section, the two end segments 7, 10 each subtend an end wall 14 sealing half the tube cross-section. The end segments 7, 10 each are fitted with a rounded end wall 15 in the end zones of the cropped portions, said end wall 15 allowing a pivoting motion tightly in front of the opposite end wall 14.

A hollow axle 16 of which the axis is perpendicular to the longitudinal axis of the end part 3 is affixed to the joint wall 13 of the end part 3 and passes through a matching aperture 17 in the joint wall 12 of the end segment 7 on the main part side and, in the joint's assembled state, is connected to a flange part 18 which constitutes a detachable upper element of the hollow axle 16, 18 and which, in the connected position, rests from above in sliding manner with a slightly larger outside diameter on the joint wall 12 of the end segment 7.

When assembled, the two components 16 and 18 of the hollow axle are connected by screwing the shown three screws 19 into threaded boreholes 20.

In the embodiment shown, an irregularly shaped aperture 21 passes through the hollow axle's two parts 16 and 18 and therefore, in the assembled state, connects the hollow space in the main part 2 to the hollow space in the distal end part 3 of the endoscope stem 1.

In order to provide screwdriver access to the screws 19 during assembly, the semi-circular cross-sectional portion of the wall of the end segment 7 is designed as a detachable cover 22 which, following joint assembly, is applied to the endoscope and illustratively is made sealing by welding the edges.

A single seal in the form of an O-ring 23 is used to seal the joint and is configured in a circumferential manner in a groove 24 in the joint wall 13 of the end part 3, and assures sealing between the joint walls 12 and 13 around the hollow axle 16.

In this manner, the invention offers a joint 4 that, as indicated in FIG. 1, allows pivoting the end part 3 about the joint 4 relative to the main part 2.

A circumferential groove 25 is present in the flange part 18 of the hollow axle 16, 18 to control pivoting, a control cable looping said groove being controlled by omitted drive means at the proximal end region of the stem 1 to drive the end part 3.

In its partly sectional end zone of the end part 3, FIG. 1 shows a fiber light guide 27 terminating within said part's tube 8 and allowing illumination from the end face of this part 3. The said end face also is fitted with a glass window 28 in front of the schematically shown optics 29 allowing the schematically shown video camera 30 to observe the region in front of said end face. A cable 31 is connected to the video camera 30.

The fiber light guide 27 and the cable 31 run jointly in a proximal direction through the tube 8 of the end part 3 into the inner space of the end segment 10 at the side of said end part and from there through the aperture 21 of the hollow axle 16, 18 into the inside space of the end segment 7 on the side of said main part and from there through the main part's tube 5 as far as the proximal end zone of the stem 1 wherein they may be connected in a manner known per se to illumination power supplies and a video observing device.

Figure 3:
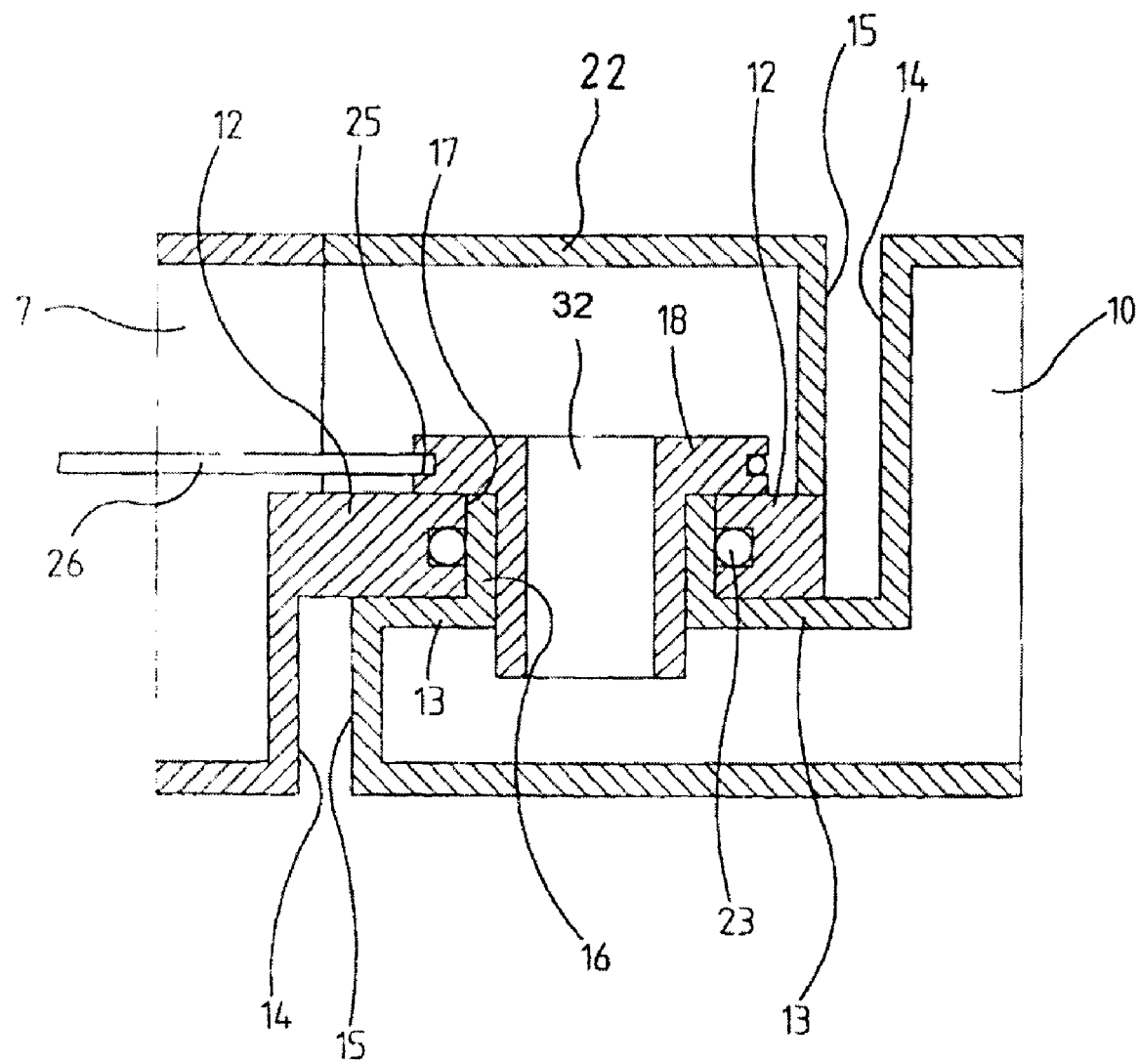
FIG. 3 is a section along line 3-3 of FIG. 1.

FIG. 3 shows a section along line 3-3 of FIG. 1 of an embodiment mode slightly differing from that of FIG. 2. Where possible, the same references are used as for FIGS. 1 and 2.

In the embodiment mode of FIG. 3, the hollow axle 16 is an internally threaded tube stub. An externally threaded hollow bolt 32 is screwed in from above. The hollow bolt 32 is fitted with the flange 18 which is looped in turn by the control cable 26 in its groove 25. After removing the detachable cover 22, the hollow bolt 32 may be loosened for purposes of disassembly.

The O-ring seal 23 of FIG. 3 also is configured in a manner different from that of the embodiment mode of FIG. 2. The aperture 17 crossed by the hollow axle 16 in the joint wall 12—which is thicker in this embodiment mode—of the end segment 7 on the main part side comprises a groove receiving the O-ring seal 23 as indicated by FIG. 3. The O-ring seal 23 runs in sealing manner on the outside of the hollow axle 16.

The invention claimed is:

1. A medical endoscope comprising:
   a stem having a main part and a distal end part;
   a video camera received in the distal end part; and
   connecting lines running through inside spaces of the stem from a proximal end region to the distal end part;
   wherein the distal end part is pivotably adjustable relative to the main part of the stem,
   wherein the main part and the distal end part are enclosed in a sealing manner by rigid stem tubes, which are supported in an abutting and sealing manner in a joint by means of a hollow axle running perpendicularly to the main part and the distal end part of the stem, and
   wherein the connecting lines running through the inside spaces of the main part and the distal end part pass through the hollow axle.

2. The endoscope as claimed in claim 1, wherein the main part and the distal end part each subtend end segments at the joint that have flat joint walls, said flat joint walls being mutually abutting and being crossed by the hollow axle.

3. The endoscope as claimed in claim 2, wherein an O-ring seal is mounted between the joint walls and configured around the hollow axle.

4. The endoscope as claimed in claim 2, wherein the hollow axle is affixed to one of the joint walls and crosses the other of the joint walls at an aperture and internally rests against the said other of the joint walls by means of an external flange.

5. The endoscope as claimed in claim 4, wherein the hollow axle is transversely split and connected by a longitudinal screw system.

6. The endoscope as claimed in claim 5, wherein the screw system is accessible from a flange end of the hollow axle and wherein a wall portion of one of the end segments may be deposited above the flange end of the hollow axle following connection of the hollow axle by the longitudinal screw system.

7. The endoscope as claimed in claim 5, wherein the external flange constitutes the head of a hollow bolt having an outer thread that can be screwed into an inside thread of the hollow axle.

8. The endoscope as claimed in claim 4, wherein the external flange is configured in the end segment of the main part and comprises a circumferential groove looped by a control cable operated from the proximal end region of the stem.

9. The endoscope as claimed in claim 2, wherein the end segments each are designed as a separate component connected to the respective rigid end tubes.

* * * * *